US011576856B2

(12) United States Patent
Spasoff et al.

(10) Patent No.: US 11,576,856 B2
(45) Date of Patent: Feb. 14, 2023

(54) METHOD FOR MAKING INJECTABLE PHARMACEUTICAL COMPOSITIONS

(71) Applicant: AMGEN INC., Thousand Oaks, CA (US)

(72) Inventors: Andrew Phillip Spasoff, Rockville, MD (US); Susanne Therese Atkinson, Dublin (IE); Adrian Bennis, Dublin (IE); Erwin Freund, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 81 days.

(21) Appl. No.: 17/050,019

(22) PCT Filed: Apr. 2, 2019

(86) PCT No.: PCT/US2019/025420

§ 371 (c)(1),
(2) Date: Oct. 23, 2020

(87) PCT Pub. No.: WO2019/209473

PCT Pub. Date: Oct. 31, 2019

(65) Prior Publication Data

US 2021/0093554 A1 Apr. 1, 2021

Related U.S. Application Data

(60) Provisional application No. 62/661,929, filed on Apr. 24, 2018.

(51) Int. Cl.

| | |
|---|---|
| ***A61K 9/00*** | (2006.01) |
| ***G01N 15/10*** | (2006.01) |
| ***A61K 9/16*** | (2006.01) |

(52) U.S. Cl.

CPC .......... *A61K 9/0019* (2013.01); *A61K 9/1611* (2013.01); *A61K 9/1647* (2013.01); *G01N 15/10* (2013.01)

(58) Field of Classification Search

None

See application file for complete search history.

(56) References Cited

U.S. PATENT DOCUMENTS

| | | | |
|---|---|---|---|
| 4,667,016 | A | 5/1987 | Lai et al. |
| 5,824,784 | A | 10/1998 | Kinstler et al. |
| 7,217,689 | B1 | 5/2007 | Elliott et al. |
| 8,207,112 | B2 | 6/2012 | Hinderer et al. |
| 8,258,262 | B2 | 9/2012 | Kinstler et al. |
| 2008/0187595 | A1 | 8/2008 | Jordan et al. |

FOREIGN PATENT DOCUMENTS

| | | | |
|---|---|---|---|
| WO | WO-2011132201 | A1 | 10/2011 |
| WO | 2012/012388 | A2 | 1/2012 |
| WO | 2014/011672 | A1 | 1/2014 |

OTHER PUBLICATIONS

Jung Young-Seok et al. "Temperature-modulated noncovalent interaction controllable complex for the long-term delivery of etanercept to treat rheumatoid arthritis". 2013 as cited on IDS.*

International Application No. PCT/US19/25420, International Preliminary Reporton Patentability, dated Nov. 5, 2020.

International Application No. PCT/US19/25420, International Search Report and Written Opinion, dated Sep. 30, 2019.

Jung et al., Temperature-modulated noncovalent interaction controllable complex for the long-term delivery of etanercept to treat rheumatoid arthritis, J. Control Release, 171(2)1143-151 (2013).

Singh et al., An industry perspective on the monitoring of subvisible particles as a quality attribute for protein therapeutics, J. Pharm. Sci., 99(8)13302-3321 (2010).

* cited by examiner

*Primary Examiner* — Danah Al-Awadi

(74) *Attorney, Agent, or Firm* — Marshall, Gerstein & Borun LLP

(57) ABSTRACT

The invention relates to methods for making injectable pharmaceutical compositions wherein particles present in the compositions are detected and analyzed, and the acceptance of the compositions is determined based on chemical and physical properties as well as toxicology and patient risks associated of the particles.

8 Claims, 3 Drawing Sheets

METHOD FOR MAKING INJECTABLE PHARMACEUTICAL COMPOSITIONS

CROSS-REFERENCE TO RELATED APPLICATIONS

This application claims the benefit of U.S. Provisional Application No. 62/661,929, filed on Apr. 24, 2018, which is hereby incorporated by reference.

FIELD OF THE INVENTION

The invention relates to methods for making injectable pharmaceutical compositions. In particular, the invention relates to methods for detecting and analyzing particles in an injectable pharmaceutical composition and determining whether the composition is acceptable.

BACKGROUND OF THE INVENTION

Injectable pharmaceutical compositions include solutions suitable for intravenous, intramuscular and subcutaneous administration. Manufacture processes for making these compositions may introduce particles to the compositions from extrinsic sources such as the manufacturing environment, equipment and packaging, and/or intrinsic sources such as the excipients used for making the compositions. Due to potential health risks that particles may have on patients (e.g., injection site reactions), particle control strategies have been implemented in manufacturing processes based on current regulatory expectations. These include implementing particle control approaches to reduce particle contamination during manufacture as well as inspecting and analyzing for the presence of particles in injectable pharmaceutical compositions at the end of manufacturing processes.

Particle control approaches include reducing particles from manufacturing equipment and manufacturing environments. The art has developed and adopted inspection and quality control strategies to ensure injectable pharmaceutical compositions meet acceptable particle levels. Once injectable pharmaceutical compositions are manufactured, they are inspected for the presence of particles. The art has also adopted standards for acceptable particle levels. For example, the US Pharmacopeia recommends that particles may be observed in no more than a specified number of drug product units, as determined by a statically justified sampling plan, when inspected under specific conditions. However, current particle control and inspection strategies do not take into consideration the safety or toxicology information associated with particles. There is a need for developing particle control strategies that take into consideration the impact of particles on patient safety.

SUMMARY OF THE INVENTION

Provided herein are methods for making injectable pharmaceutical composition by leveraging information of particles historically detected in injectable compositions (e.g., size and materials composition of particles) and the corresponding toxicology and safety evaluations on patients. In one aspect, the invention disclosed herein comprises a method of making an injectable pharmaceutical composition comprising etanercept, the method comprises detecting the presence of one or more particles in the composition, analyzing the size of the particles and the materials comprised in the particles, and accepting the injectable pharmaceutical composition if the largest particle of the one or more particles has a size and a mass within certain range disclosed herein. In one embodiment, the invention disclosed herein comprises a method of making an injectable pharmaceutical composition comprising etanercept, the method comprises detecting the presence of one or more particles in the composition, analyzing the size of the particles and the materials comprised in the particles, and accepting the injectable pharmaceutical composition if the largest particle of the one or more particles has a length (L) of no more than about 19,200 μm, a width (W) of no more than about 2,939 μm, and a mass (M) of no more than about 97,200 μg, and wherein the one or more particles comprise acrylic, aluminum, aliphatic hydrocarbon, charcoal, borosilicate glass, wool, silk, polyester (PET), polyurethane, polyether ether, polytetrafluoroethylene (PTFE), polyoxymethylene (POM), polystyrene, silicon carbide, or stainless steel. The size and mass range of the largest particle that may be found in an injectable entanercept composition comprising each of the materials are also disclosed herein. In one embodiment, the injectable pharmaceutical composition is suitable for subcutaneous administration.

In another aspect, the invention disclosed herein comprises a method of making an injectable pharmaceutical composition comprising darbepoetin, the method comprises detecting the presence of one or more particles in the composition, analyzing the size of the particles and the materials comprised in the particles, and accepting the composition if the largest particle of the one or more particles has a L of no more than about 4,530 μm, a W of no more than about 8,890 μm, and a M of no more than about 21,190 μg, and wherein the one or more particles comprise acrylate, aluminum, cellulose, epoxy resin, keratin, hydrated aluminum silicate, magnesium, magnesium silicate, nitrocellulose, polyurethane, polytetrafluoroethylene (PTFE), stainless steel, zinc, borosilicate glass, iron, iron and nickel rich material with phosphate, polyamide, polyethylene, polyvinyl chloride (PVC), or titanium. The size and mass range of the largest particle that may be found in an injectable darbepoetin composition comprising each of the materials are also disclosed herein. In one embodiment, the injectable pharmaceutical composition comprising darbepoetin is suitable for intravenous or subcutaneous administration.

In another aspect, the invention disclosed herein comprises a method of making an injectable pharmaceutical composition comprising pegfilgrastim, the method comprises: detecting the presence of one or more particles in the composition, analyzing the size of the particles and the materials comprised in the particles, and accepting the composition if the largest particle of the one or more particles has a L of no more than about 3,500 μm, a W of no more than about 430 μm, and a M of no more than about 5,100 μg, and wherein the one or more particles comprise aluminum, calcium carbonate, iron, polytetrafluorocarbon, Poly(ethylacrylate), polystyrene, polysulfone, poly(isobutylene)-butyl rubber, rubber, silicate, silicone, or stainless steel. The size and mass range of the largest particle that may be found in an injectable pegfilgrastim composition comprising each of the materials are also disclosed herein. In one embodiment, the injectable pharmaceutical composition comprising pegfilgrastim is suitable for subcutaneous administration.

DETAILED DESCRIPTION OF THE INVENTION

Figure 1:
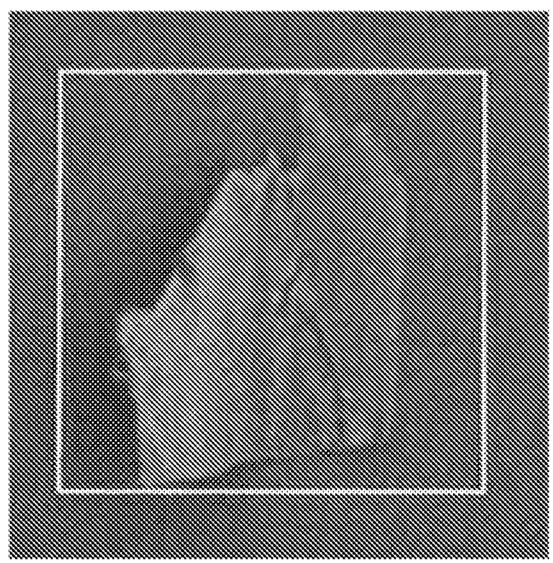
FIG. 1 shows a particle comprising acrylic in an injectable composition comprising etanercept.
Figure 2:
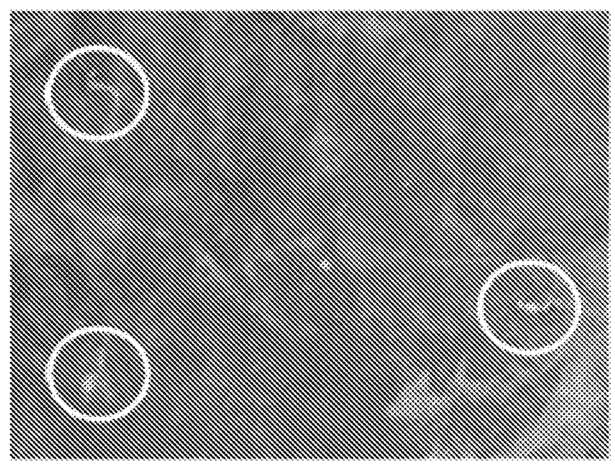
FIG. 2 shows particles comprising charcoal in an injectable composition comprising etanercept.
Figure 3:
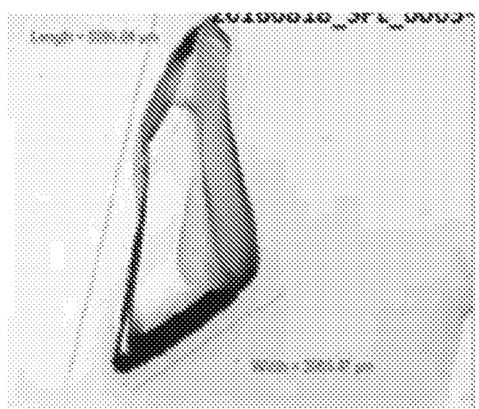
FIG. 3 shows a particle comprising borosilicate glass in an injectable composition comprising etanercept.
Figure 4:
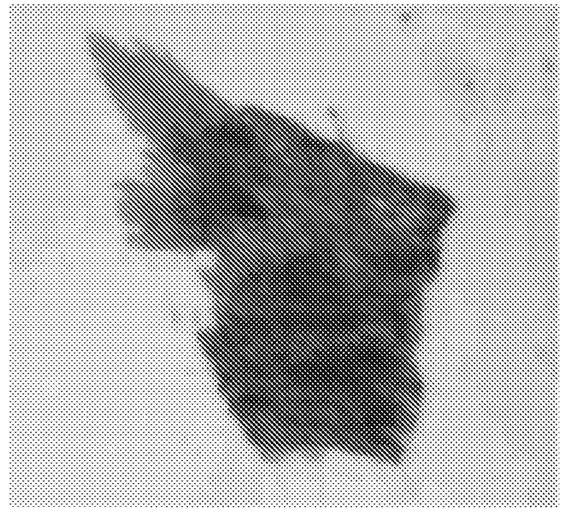
FIG. 4 shows a particle comprising acrylate in an injectable composition comprising darbepoetin.
Figure 5:
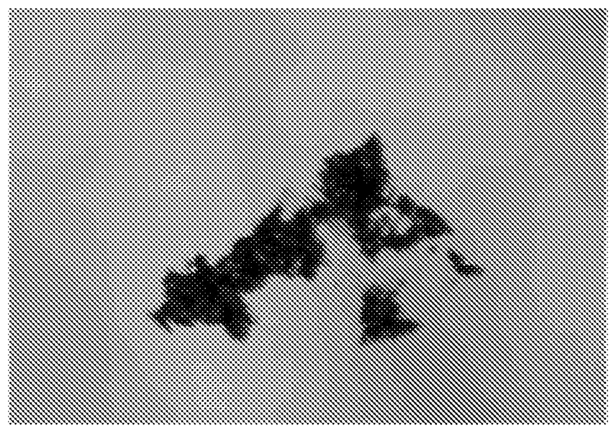
FIG. 5 shows a particle comprising aluminum in an injectable composition comprising darbepoetin.
Figure 6:
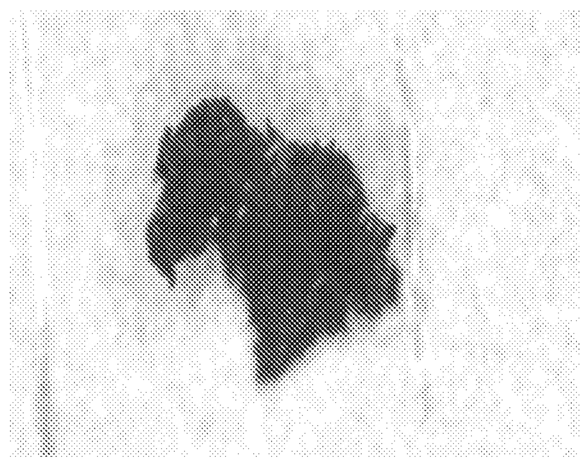
FIG. 6 shows a particle comprising calcium carbonate in an injectable composition comprising pegfilgrastim.
Figure 7:
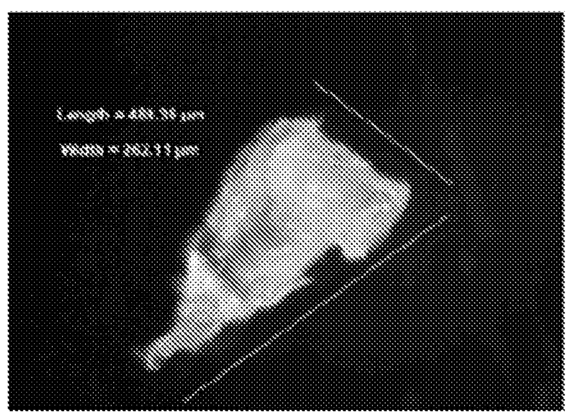
FIG. 7 shows a particle comprising polystyrene in an injectable composition comprising pegfilgrastim.
Figure 8:
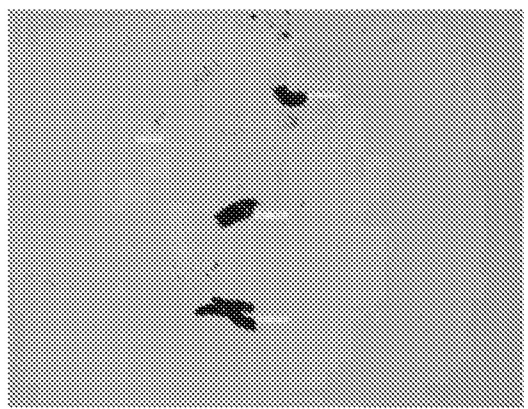
FIG. 8 shows a particle comprising iron in an injectable composition comprising pegfilgrastim.

Disclosed herein are methods for making injectable pharmaceutical composition comprising an active ingredient, the method comprises detecting the presence of one or more particles in the composition, analyzing the size of the particles and materials comprised in the particles, and accepting the composition if the largest particle of the one or more particles has a size and mass within a certain range. The methods disclosed herein are based on the data compiled from particles that have been observed in injectable pharmaceutical compositions historically, their size, mass and composition as well as toxicology evaluations and medical opinions of the particles on patients. It has been found that potential risks of particles to patients are low to negligible if the particles have a size and mass within a certain range.

As used herein, the term an "injectable pharmaceutical composition" refers to a formulation comprising a therapeutically active ingredient and is suitable for injection into a patient such as a human in need thereof. In certain embodiments, an injectable pharmaceutical composition is a solution substantially sterile and does not contain any agents that are unduly toxic or infectious to the recipient. Examples of injectable pharmaceutical composition include compositions suitable for subcutaneous, intramuscular, intravenous, intraperitoneal, intracardiac, intraarticular and intracavernous administration.

A therapeutically active ingredient comprised in the injectable pharmaceutical composition refers to a substance that is biologically active, has an effect in the diagnosis, cure, mitigation, treatment or prevention of disease, or in restoring, correcting or modifying physiological functions in a patient. Therapeutically active ingredients include, without limitation, small molecular compounds, polypeptides, antibodies, antigen-binding fragments, chemically modified polypeptides, polypeptides conjugated to a chemical moiety and antibodies conjugated to a chemical moiety. In some embodiments, a therapeutically active ingredient comprised in the injectable pharmaceutical composition is a polypeptide, a chemically modified polypeptide, a polypeptide conjugated to a chemical moiety, an antibody and an antigen-binding fragment, more specifically, a polypeptide, a polypeptide conjugated to a chemical moiety or an antibody. In certain embodiments, the therapeutically active ingredient comprised in the injectable pharmaceutical composition is etanercept, an erythropoiesis-stimulating protein such as erythropoietin and darbepoetin, or pegfilgrastim.

Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. When expressed in mammalian cells, it forms a homodimeric complex with two domains of the TNF receptor. Thus, it is an artificial protein that is different from both antibodies and soluble TNF receptors, and therefore subject to different degradation pathways than either. Etanercept is commercially available as Enbrel® (Amgen Inc., Thousand Oaks, Calif.) and is approved to treat moderately to severely active rheumatoid arthritis, moderately to severely active polyarticular juvenile idiopathic arthritis (JIA) in patients ages 2 and older, chronic moderate to severe plaque psoriasis (PsO) in adults, psoriatic arthritis (PsA) in adults, and active ankylosing spondylitis (AS). Etanercept is commercially available in a lyophilized formulation to be reconstituted immediately before injection or as a solution in a pre-filled syringe or cartridge.

Erythropoietin, also known as EPO, is a glycoprotein protein that stimulates red blood cell production. Erythropoietin as used herein includes human erythropoietin purified from natural sources (e.g., urine), produced by recombinant DNA technology in eukaryotic host cells (rHuEPO) (e.g., U.S. Pat. No. 4,667,016, hereby incorporated by reference) as well as biologically active analogs thereof. Suitable eukaryotic hosts include yeast (e.g., *S. cerevisiae*) and mammalian (e.g., Chinese hamster ovary (CHO)) cells. Depending upon the host employed, the EPO expression product may be glycosylated with mammalian or other eukaryotic carbohydrates, or it may be non-glycosylated.

Human erythropoietin has 166 amino acid residues. Both human urinary derived erythropoietin and recombinant erythropoietin (expressed in mammalian cells) have amino acids 1-165 of the amino acid sequence of human erythropoietin and contain three N-linked and one O-linked oligosaccharide chains. N-linked glycosylation occurs at asparagine residues located at positions 24, 38 and 83 while O-linked glycosylation occurs at a serine residue located at position 126.

EPO analogs useful in the practice of this invention include those having one or more amino acid additions, substitutions, and/or deletions as compared to either naturally-derived or rHuEPO. Particularly useful analogs including substitution analogs such as those disclosed in U.S. Pat. No. 7,217,689 (hereby incorporated by reference) that provide additional sites for glycosylation as compared to either naturally-derived or rHuEPO.)

In a particular embodiment, an EPO analog is darbepoetin produced in CHO cells by recombinant DNA technology. Darbepoetin contains amino acid residues 1-165 of human erythropoietin and five N-linked oligosaccharide chains with an approximate molecular weight of 37,000 daltons. The two additional N-glycosylation sites of darbepoetin result from amino acid substitutions in the human erythropoietin polypeptide. Darbepoetin is commercially available as Aranesp® (Amgen Inc., Thousand Oaks, Calif.) and is formulated as a sterile, colorless, preservative-free solution for intravenous or subcutaneous administration. Darbepoetin is approved to treat anemia due to chronic kidney disease or due to chemotherapy in patients with cancer.

Pegfilgrastim is a covalent conjugate of recombinant methionyl filgrastim and monomethoxypolyethylene glycol. Filgrastim is a 175 amino acid human granulocyte colony stimulating factor (G-CSF) produced by recombinant DNA technology in *E. coli*. The amino acid sequence of filgrastim is identical to the 174 amino acid species of human G-CSF with the addition of an N-terminal methionine necessary for expression. Filgrastim has a molecular weight of approximately 19 kilodaltons (kD).

Pegfilgrastim is produced by covalently linking a 20 kD monomethoxypolyethylene glycol molecule to the N-terminal methionine residue of filgrastim (e.g., as disclosed in U.S. Pat. Nos. 5,824,784 and 8,258,262, incorporated herein in its entirety). The average molecular weight of pegfilgrastim is approximately 39 kD. Pegfilgrastim is commercially available as Neulasta® (Amgen Inc., Thousand Oaks, Calif.) and is formulated as a sterile, clear, colorless, preservative-free solution in a prefilled syringe or an on-body injector for subcutaneous administration.

Pegfilgrastim is approved to decrease the incidence of infection, as manifested by febrile neutropenia, in patients with non-myeloid malignancies receiving myelosuppressive anti-cancer drugs associated with a clinically significant incidence of febrile neutropenia and to increase survival in patients acutely exposed to myelosuppressive doses of radiation.

As used herein, the term "particle" refers to mobile, undissolved matters present in an injectable pharmaceutical composition such as an injectable solution. Generally, a particle can be described by its physical and chemical properties. Physical properties include size (e.g., length, width, height) and mass of the particle, while chemical properties include the materials comprised in the particle. Particles with a size of 50 μm or larger may be visible to human eye. Methods disclosed herein are generally applicable to detecting and analyzing particles of all sizes, in particular visible particles.

Particles present in an injectable pharmaceutical composition may come from various sources including extrinsic and intrinsic sources. Extrinsic sources include the manufacturing environment, manufacturing equipment and packaging materials. Intrinsic sources include excipients used for making the injectable pharmaceutical composition. In addition, therapeutically active ingredients such as polypeptides and antibodies can aggregate and form particles. It is understood that methods disclosed herein are particularly suitable for making injectable pharmaceutical compositions wherein the particles are from extrinsic and/or intrinsic sources other than the therapeutically active ingredient comprised in the compositions.

Nonlimiting exemplary materials from extrinsic and intrinsic sources that may be comprised in particles include acrylic, acrylate, aluminum, aluminum silicate, aliphatic hydrocarbon, borosilicate glass, calcium carbonate, cellulose, charcoal, epoxy resin, iron, iron and nickel rich material with phosphate, hydrated aluminum silicate, keratin, magnesium, magnesium silicate, natural protein fiber (wool and silk), nitrocellulose, polyester (PET), polyamide, polyether ether Ketone, polyethylacrylate, polyethylene, poly(isobutylene-butyl) rubber, polyoxymethylene (POM), polystyrene, polysulfone, polytetrafluorocarbon, polytetrafluoroethylene (PTFE), polyurethane, polyvinyl chloride (PVC), rubber, silicate, silicon carbide, silicone, stainless steel, titanium, and zinc. A particle may comprise any one or a combination of these materials.

The method disclosed herein is based on data and information collected from particles historically found in injectable pharmaceutical compositions during inspection and the investigation and evaluation of potential safety risks of the particles on patients based on the data and information. Specifically, the data and information include forensic data on particles, including product the particles were observed, chemical and physical properties of the largest particle that has been identified (e.g., materials comprised in the largest particle, its dimensions and mass), and optionally, an image representative of the particle. The forensic data along with evaluation criteria such as product's route of administration, potential source of the particle, patient population, toxicology assessment and medical opinion are used to evaluate the potential patient safety risk of the particles.

Chemical and physical properties of particles (e.g., size, mass and materials comprised in the particles) can be measured and/or calculated using various methods known to one of ordinary skill in the art. These methods will be described below. The toxicology assessment determines patient safety impact from a toxicological perspective and is based on the materials comprised in particles and the mass of particles. The medical opinion assesses elements including the outcome of the toxicology assessment, the product dosage, route of administration, impact to sterility assurance and the likely particle source, to determine the potential patient safety impact of particles.

Based on the investigation, assessment and evaluation, it has been found that particles having chemical and physical properties within certain parameters raise little toxicological concern and pose low to negligible safety risk when administered to patients. The presence of such particles in an injectable pharmaceutical composition is thus deemed to be acceptable. The invention disclosed herein leverages the knowledge of potential patient safety risks associated with particles historically found in injectable pharmaceutical compositions to determine whether or not accepting an injectable pharmaceutical composition under inspection if a particle is found in the composition.

Consequently, the invention disclosed herein provides a method for making an injectable pharmaceutical composition comprising a therapeutically active ingredient, the method comprises detecting the presence of one or more particles in the composition, analyzing the size and mass of the particles, and accepting the composition if the largest particle of the one or more particles has a size (e.g., length (L), width (W), height (H)) and mass (M) within a certain range. In specific embodiments, the therapeutically active ingredient is etanercept, darbepoetin or pegfilgrastim.

As used herein, the term "length (L)" refers to the longest dimension of a particle measured end to end. The term "width (W)" refers to the second longest dimension of a particle measured end to end. The term "height (H)" refers to the third longest dimension of a particle measured from end to end. Mass is calculated based on the volume of the particle and the density of the material(s) comprised in the particle. Methods for detecting the presence of particles in an injectable composition and measuring the size and calculating the mass of a particle will be described below.

Injectable Pharmaceutical Compositions Comprising Etanercept

In some embodiments, the injectable pharmaceutical composition comprises etanercept. In one embodiment, particles that may be found in an etanercept composition comprise any one of the following: acrylic, aluminum, aliphatic hydrocarbon, charcoal, borosilicate glass, natural protein fiber (wool and silk), polyester (PET), polyurethane, polyether ether ketone, polytetrafluoroethylene (PTFE), polyoxymethylene (POM), polystyrene, silicon carbide, and stainless steel. In one embodiment, particles found in an etanercept composition comprise any one of acrylic, aluminum, aliphatic hydrocarbon, borosilicate glass, charcoal, polyurethane, polytetrafluoroethylene (PTFE), silicon carbide, or stainless steel. In one embodiment, particles found in an etanercept composition comprise any one of acrylic, charcoal, or borosilicate glass.

One or more particles may be found in an injectable etanercept composition. The composition is acceptable as long as the size (e.g., length, width) and mass of the largest particle of the one or more particles are within a certain range. Exemplary size and mass of the largest particle that may be acceptable in an etanercept composition include that the particle has a L of no more than about 19,200 μm, a W of no more than about 2,939 μm, and a M of no more than about 39,300 μg; or that the particle has a L of no more than about 6,154 μm, a W of no more than about 2,454 μm, and a M of no more than about 39,300 μg; or that the particle has a L of no more than about 5,047 μm, a W of no more than about 2,939 μm, and a M of no more than about 97,200 μg; or that the particle has a L of no more than about 700 μm, a W of no more than about 400 μm, and a M of no more than about 72 μg; or that the particle has a L of no more than about 257 μm, a W of no more than about 133 μm, and a M of no more than about 5.4 μg; or that the particle has a L of no more than about 176 μm, a W of no more than about 110 μm, and a M of no more than about 2.9 μg; or that the particle has a L of no more than about 420 μm, a W of no more than about 225 μm, and a M of no more than about 0.001 μg; or that the particle has a L of no more than about 131 μm, a W of no more than about 64 μm, and a M of no more than about 0.42 μg; or that the particle has a L of no more than about 19,200 μm, a W of no more than about 50 μm, and a M of no more than about 50 μg; or that the particle has a L of no more than about 2,388 μm, a W of no more than about 67 μm, and a M of no more than about 14.7 μg; or that the particle has a L of no more than about 359 μm, a W of no more than about 306 μm, and a M of no more than about 21 μg; or that the particle has a L of no more than about 5,150 μm, a W of no more than about 300 μm, and a M of no more than about 2,330 μg; or that the particle has a L of no more than about 700 μm, a W of no more than about 250 μm, and a M of no more than about 45.9 μg; or that the particle has a L of no more than about 1,891 μm, a W of no more than about 596.8 μm, and a M of no more than about 1,010 μg; or that the particle has a L of no more than about 359 μm, a W of no more than about 306 μm, and a M of no more than about 48.7 μg; or that the particle has a L of no more than about 450 μm, a W of no more than about 400 μm, and a M of no more than about 72 μg.

In some embodiments, the invention disclosed herein comprises a method of making an injectable pharmaceutical composition comprising etanercept, the method comprises detecting the presence of one or more particles in the composition, analyzing the size of the particles and the materials comprised in the particles, and accepting the injectable pharmaceutical composition if the largest particle of the one or more particles has a L of no more than about 19,200 μm, a W of no more than about 2,939 μm, and a M of no more than about 97,200 μg, and the one or more particles comprise acrylic, aluminum, aliphatic hydrocarbon, charcoal, borosilicate glass, natural protein fiber (wool and silk), polyester (PET), polyurethane, polyether ether, polytetrafluoroethylene (PTFE), Polyoxymethylene (POM), Polystyrene, silicon carbide, or stainless steel. In some embodiments, the method comprises detecting the presence of one or more particles in the composition, analyzing the size of the particles and the materials comprised in the particles, and accepting the injectable pharmaceutical composition if the largest particle of the one or more particles has a L of no more than about 700 μm, a W of no more than about 400 μm, and a M of no more than about 72 μg, and the one or more particles comprise acrylic, aluminum, aliphatic hydrocarbon, charcoal, polyurethane, polytetrafluoroethylene (PTFE), silicon carbide, or stainless steel. In some embodiments, the method comprises detecting the presence of one or more particles in the composition, analyzing the size of the particles and the materials comprised in the particles, and accepting the injectable pharmaceutical composition if the largest particle of the one or more particles has a L of no more than about 6,154 μm, a W of no more than about 2,454 μm, and a M of no more than about 39,300 μg, and wherein the one or more particles comprise polyether ether ketone, POM, or polystyrene.

In some embodiments of the method, the injectable composition comprising etanercept is acceptable if the largest particle of the one or more particles found in the composition has a L of no more than about 257 μm, a W of no more than about 133 μm, and a M of no more than about 5.4 μg, and the one or more particles comprise acrylic. In some embodiments of the method, the injectable composition comprising etanercept is acceptable if the largest particle of the one or more particles found in the composition has a L of no more than about 5,047 μm, a W of no more than about 2,939 μm, and a M of no more than about 97,200 μg, and the one or more particles comprise borosilicate glass. In some embodiments of the method, the injectable composition comprising etanercept is acceptable if the largest particle of the one or more particles found in the composition has a L of no more than about 176 μm, a W of no more than about 110 μm, and a M of no more than about 2.9 μg, and the one or more particles comprise charcoal. In some embodiments of the method, the injectable composition comprising etanercept is acceptable if the largest particle of the one or more particles found in the composition has a L of no more than about 420 μm, a W of no more than about 225 μm, and a M of no more than about 0.001 μg, and the one or more particles comprise aluminum. In some embodiments of the method, the injectable composition comprising etanercept is acceptable if the largest particle of the one or more particles found in the composition has a L of no more than about 131 μm, a W of no more than about 64 μm, and a M of no more than about 0.42 μg, and the one or more particles comprise aliphatic hydrocarbon. In some embodiments of the method, the injectable composition comprising etanercept is acceptable if the largest particle of the one or more particles found in the composition has a L of no more than about 19,200 μm, a W of no more than about 50 μm, and a M of no more than about 50 μg wool and no more than about 50 μg silk, and the one or more particles comprise natural protein fiber (wool and silk). In some embodiments of the method, the injectable composition comprising etanercept is acceptable if the largest particle of the one or more particles found in the composition has a L of no more than about 2,388 μm, a W of no more than about 67 μm, and a M of no more than about 14.7 μg, and the one or more particles comprise polyester. In some embodiments of the method, the injectable composition comprising etanercept is acceptable if the largest particle of the one or more particles found in the composition has a L of no more than about 359 μm, a W of no more than about 306 μm, and a M of no more than about 21 μg, and the one or more particles comprise polyurethane. In some embodiments of the method, the injectable composition comprising etanercept is acceptable if the largest particle of the one or more particles found in the composition has a L of no more than about 5,150 μm, a W of no more than about 300 μm, and a M of no more than about 2,330 μg, and the one or more particles comprise polyether ether ketone. In some embodiments of the method, the injectable composition comprising etanercept is acceptable if the largest particle of the one or more particles found in the composition has a L of no more than about 700 μm, a W of no more than about 250 μm, and a M of no more than about 45.9 μg, and the one or more particles comprise PTFE. In some embodiments of the method, the injectable composition comprising etanercept is acceptable if the largest particle of the one or more particles found in the composition has a L of no more than about 1,891 μm, a W of no more than about 596.8 μm, and a M of no more than about 1,010 μg, and the one or more particles comprise POM. In some embodiments of the method, the injectable composition comprising etanercept is acceptable if the largest particle of the one or more particles found in the composition has a L of no more than about 6,154 μm, a W of no more than about 2,454 μm, and a M of no more than about 39,300 μg, and the one or more particles comprise polystyrene. In some embodiments of the method, the injectable composition comprising etanercept is acceptable if the largest particle of the one or more particles found in the composition has a L of no more than about 359 μm, a W of no more than about 306 μm, and a M of no more than about 48.7 μg, and the one or more particles comprise silicon carbide. In some embodiments of the method, the injectable composition comprising etanercept is acceptable if the largest particle of the one or more particles found in the composition has a L of no more than about 450 μm, a W of no more than about 400 μm, and a M of no more than about 72 μg, and the one or more particles comprise stainless steel.

As used herein, the term "about" is understood to mean that there can be variation in a given value, including a range that is 5%, 10%, 15% or 20% above and below the given value.

Particles comprising different material may have different size and mass range for the largest acceptable particle. For example, the largest acceptable particle comprising acrylic that may be found in an etanercept composition can have an L, W and M of no more than about 257 μm, about 133 μm, and about 5.4 μg, respectively, while the largest acceptable particle comprising charcoal that may be found in an etanercept composition can have an L, W, and M of no more than about 176 μm, about 110 μm, and about 2.9 μg, respectively. Specific examples of the types of particles that may be found in an etanercept injectable composition, the size and mass of the largest acceptable particle for each type as well as the toxicology assessment and medical opinion of the largest acceptable for each type are shown in Example 1 below.

In some embodiments of the method, different particles of the one or more particles identified in the composition comprising etanercept may comprise different types materials, e.g., some particles of the one or more particles comprise acrylic and some particles of the one or more particles comprise charcoal, the composition is acceptable if the largest particle of each type has a L, W and M that is within the range disclosed herein for that type of particle, e.g., the largest of the acrylic particles has a L of no more than about 257 μm, a W of no more than about 133 μm, and a M of no more than about 5.4 μg, and the largest of the charcoal particles has a L of no more than about 176 μm, a W of no more than about 110 μm, and a M of no more than about 2.9 μg.

In one embodiment, the injectable pharmaceutical composition comprising etanercept is a lyophilized formulation to be reconstituted immediately before subcutaneous administration. In another embodiment, the injectable pharmaceutical composition comprising etanercept is a solution in a single-use vial, or a pre-filled syringe or cartridge for subcutaneous administration. In another embodiment, the injectable pharmaceutical composition comprising etanercept comprises a buffer. In another embodiment, the injectable pharmaceutical composition comprising etanercept is a buffer-free formulation.

Injectable Pharmaceutical Compositions Comprising Darbepoetin

In some embodiments, the injectable pharmaceutical composition comprises darbepoetin. In one embodiment, particles that may be found in a darbepoetin composition comprise any one of acrylate, aluminum, borosilicate glass, cellulose, epoxy resin, keratin, hydrated aluminum silicate, iron, iron and nickel rich material with phosphate, magnesium, magnesium silicate, nitrocellulose, polyurethane, polytetrafluoroethylene (PTFE), polyamide, polyethylene, polyvinyl chloride (PVC), stainless steel, zinc, or titanium. In one embodiment, particles that may be found in a darbepoetin composition comprise any one of acrylate, aluminum, cellulose, epoxy resin, keratin, hydrated aluminum silicate, magnesium, magnesium silicate, nitrocellulose, polyurethane, polytetrafluoroethylene (PTFE), iron, iron and nickel rich material with phosphate, stainless steel, or zinc. In one embodiment, particles that may be found in a darbepoetin composition comprise any one of acrylate, aluminum, cellulose, epoxy resin, hydrated aluminum silicate, magnesium, nitrocellulose, polytetrafluoroethylene (PTFE), iron, or zinc. In one embodiment, particles that may be found in a darbepoetin composition comprise acrylate, aluminum, or cellulose.

One or more particles may be found in an injectable darbepoetin composition. The composition is acceptable as long as the size (e.g., length and width) and mass of the largest particle of the one or more particles are within a certain range. Exemplary size and mass of the largest particle that may be acceptable in a darbepoetin composition include that the particle has a L of no more than about 4,530 μm, a W of no more than about 8,890 μm, and a M of no more than about 21,190 μg; or that the particle has a L of no more than about 904 μm, a W of no more than about 509 μm, and a M of no more than about 398 μg; or that the particle has a L of no more than about 836 μm, a W of no more than about 390 μm, and a M of no more than 64.2 μg; or that the particle has a L of no more than about 775 μm, a W of no more than about 184 μm, and a M of no more than about 212 μg; or that the particle has a L of no more than about 302 μm, a W of no more than about 184 μm, and a M of no more than 11 μg; or that the particle has a L of no more than about 74 μm, a W of no more than about 28 μm, and a M of no more than 0.14 μg; or that the particle has a L of no more than about 775 μm, a W of no more than about 43 μm, and a M of no more than 1.7 μg; or that the particle has a L of no more than about 442 μm, a W of no more than about 237 μm, and a M of no more than about 60 μg; or that the particle has a L of no more than about 2,304 μm, a W of no more than about 1,790 μm, and a M of no more than about 21,190 μg; or that the particle has a L of no more than about 904 μm, a W of no more than about 10 μm, a H of no more than 412 μm, and a M of no more than about 3 μg iron, no more than about 19 μg nickel, and no more than about 6.6 μg phosphate; or that the particle has a L of no more than about 81 μm, a W of no more than about 44 μm, and a M of no more than about 212 μg; or that the particle has a L of no more than about 515 μm, a W of no more than about 509 μm, and a M of no more than about 357.8 μg; or that the particle has a L of no more than about 74 μm, a W of no more than about 28 μm, and a M of no more than about 0.14 μg; or that the particle has a L of no more than about 836 μm, a W of no more than about 120 μm, and a M of no more than about 1

μg; or that the particle has a L of no more than about 681 μm, a W of no more than 390 μm, and a M of no more than about 398 μg; or that the particle has a L of no more than about 471 μm, a W of no more than about 333 μm, and a M of no more than about 64.2 μg; or that the particle has a L of no more than about 1,331 μm, a W of no more than about 293 μm, and a M of no more than about 130 μg; or that the particle has a L of no more than about 570 μm, a W of no more than about 321 μm, and a M of no more than about 130 μg; or that the particle has a L of no more than about 4,530 μm, a W of no more than about 8,890 μm, and a M of no more than about 764 μg; or that the particle has a L of no more than about 129 μm, a W of no more than about 93 μm, and a M of no more than about 2.4 μg; or that the particle has a L of no more than about 1,265 μm, a W of no more than about 322 μm, and a M of no more than about 181 μg; or that the particle has a L of no more than about 254 μm, a W of no more than about 190 μm, and a M of no more than about 72.9 μg; or that the particle has a L of no more than about 1,331 μm, a W of no more than about 174 μm, and a M of no more than about 926 μg; or that the particle has a L of no more than about 836 μm, a W of no more than about 120 μm, and a M of no more than about 4.3 μg.

In some embodiments, the invention disclosed herein comprises a method of making an injectable pharmaceutical composition comprising darbepoetin, the method comprises detecting the presence of one or more particles in the composition, analyzing the size of the particles and the materials comprised in the particles, and accepting the injectable pharmaceutical composition if the largest particle of the one or more particles has a L of no more than about 4,530 μm, a W of no more than about 8,890 μm, and a M of no more than about 21,190 μg, and the one or more particles comprise acrylate, aluminum, cellulose, epoxy resin, keratin, hydrated aluminum silicate, magnesium, magnesium silicate, nitrocellulose, polyurethane, polytetrafluoroethylene (PTFE), stainless steel, zinc, borosilicate glass, iron, iron and nickel rich material with phosphate, polyamide, polyethylene, polyvinyl chloride (PVC), or titanium. In some embodiments of the method, the injectable composition comprising darbepoetin is acceptable if the largest particle of the one or more particles has a L of no more than about 904 μm, a W of no more than about 509 μm, and a M of no more than about 398 μg, and the one or more particles comprise acrylate, aluminum, cellulose, epoxy resin, keratin, hydrated aluminum silicate, magnesium, magnesium silicate, nitrocellulose, polyurethane, polytetrafluoroethylene (PTFE), stainless steel, zinc, iron, or iron and nickel rich material with phosphate. In some embodiments of the method, the injectable composition comprising darbepoetin is acceptable if the largest particle of the one or more particles has a L of no more than about 836 μm, a W of no more than about 390 μm, and a M of no more than about 64.2 μg, and the one or more particles comprise acrylate, aluminum, cellulose, epoxy resin, magnesium, nitrocellulose, polytetrafluoroethylene (PTFE), stainless steel, iron, or zinc.

In some embodiments of the method, the injectable composition comprising darbepoetin is acceptable if the largest particle of the one or more particles found in the composition has a L of no more than about 302 μm, a W of no more than about 184 μm, and a M of no more than 11 μg, and the one or more particles comprise acrylate. In some embodiments of the method, the injectable composition comprising darbepoetin is acceptable if the largest particle of the one or more particles found in the composition has a L of no more than about 74 μm, a W of no more than about 28 μm, and a M of no more than 0.14 μg, and the one or more particles comprise aluminum. In some embodiments of the method, the injectable composition comprising darbepoetin is acceptable if the largest particle of the one or more particles found in the composition has a L of no more than about 479 μm, a W of no more than about 127 μm, and a M of no more than 11.6 μg, and the one or more particle comprise cellulose. In some embodiments of the method, the injectable composition comprising darbepoetin is acceptable if the largest particle of the one or more particles found in the composition has a L of no more than about 442 μm, a W of no more than about 237 μm, and a M of no more than about 60 μg, and the one or more particles comprise epoxy resin. In some embodiments of the method, the injectable composition comprising darbepoetin is acceptable if the largest particle of the one or more particles found in the composition has a L of no more than about 2,034 μm, a W of no more than about 1,790 μm, and a M of no more than about 21,190 μg, and the one or more particles comprise borosilicate glass. In some embodiments of the method, the injectable composition comprising darbepoetin is acceptable if the largest particle of the one or more particles found in the composition has a L of no more than about 904 μm, a W of no more than about 10 μm, a H of no more than about 412 μm, and a M of no more than about 3 μg iron, no more than about 19.1 μg nickel, and no more than about 6.6 μg phosphate, and the one or more particles comprise iron and nickel rich material with phosphate. In some embodiments of the method, the injectable composition comprising darbepoetin is acceptable if the largest particle of the one or more particles found in the composition has a L of no more than about 81 μm, a W of no more than about 44 μm, and a M of no more than about 212 μg, and the one or more particles comprise keratin. In some embodiments of the method, the injectable composition comprising darbepoetin is acceptable if the largest particle of the one or more particles found in the composition has a L of no more than about 515 μm, a W of no more than about 509 μm, and a M of no more than about 357.8 μg, and the one or more particles comprise hydrated aluminum silicate. In some embodiments of the method, the injectable composition comprising darbepoetin is acceptable if the largest particle of the one or more particles found in the composition has a L of no more than about 74 μm, a W of no more than about 28 μm, and a M of no more than about 0.05 μg, and the one or more particles comprise iron. In some embodiments of the method, the injectable composition comprising darbepoetin is acceptable if the largest particle of the one or more particles found in the composition has a L of no more than about 836 μm, a W of no more than about 120 μm, and a M of no more than about 1 μg, and the one or more particles comprise magnesium. In some embodiments of the method, the injectable composition comprising darbepoetin is acceptable if the largest particle of the one or more particles found in the composition has a L of no more than about 681 μm, a W of no more than about 390 μm, and a M of no more than about 398 μg, and the one or more particles comprise magnesium silicate. In some embodiments of the method, the injectable composition comprising darbepoetin is acceptable if the largest particle of the one or more particles found in the composition has a L of no more than about 471 μm, a W of no more than about 333 μm, and a M of no more than about 64.2 μg, and the one or more particles comprise nitrocellulose. In some embodiments of the method, the injectable composition comprising darbepoetin is acceptable if the largest particle of the one or more particles found in the composition has a L of no more than about 1,331 μm, a W of no more than about 293 μm, and a M of no more than about 130 μg, and the one or more particles comprise polyamide. In some embodiments of the method, the injectable composition comprising darbepoetin is acceptable if the largest particle of the one or more particles found in the composition has a L of no more than about 570 μm, a W of no more than about 321 μm, and a M of no more than about 130 μg, and the one or more particles comprise polyurethane. In some embodiments of the method, the injectable composition comprising darbepoetin is acceptable if the largest particle of the one or more particles found in the composition has a L of no more than about 4,530 μm, a W of no more than about 8,890 μm, and a M of no more than about 764 μg, and the one or more particles comprise polyethylene. In some embodiments of the method, the injectable composition comprising darbepoetin is acceptable if the largest particle of the one or more particles found in the composition has a L of no more than about 129 μm, a W of no more than about 93 μm, and a M of no more than about 2.4 μg, and the one or more particles comprise PTFE. In some embodiments of the method, the injectable composition comprising darbepoetin is acceptable if the largest particle of the one or more particles found in the composition has a L of no more than about 1,265 μm, a W of no more than about 322 μm, and a M of no more than about 181 μg, and the one or more particles comprise PVC. In some embodiments of the method, the injectable composition comprising darbepoetin is acceptable if the largest particle of the one or more particles found in the composition has a L of no more than about 254 μm, a W of no more than about 190 μm, and a M of no more than about 72.9 μg, and the one or more particles comprise stainless steel. In some embodiments of the method, the injectable composition comprising darbepoetin is acceptable if the largest particle of the one or more particles found in the composition has a L of no more than about 1,331 μm, a W of no more than about 174 μm, and a M of no more than about 926 μg, and the one or more particles comprise titanium. In some embodiments of the method, the injectable composition comprising darbepoetin is acceptable if the largest particle of the one or more particles found in the composition has a L of no more than about 836 μm, a W of no more than about 120 μm, and a M of no more than about 4.3 μg, and the one or more particles comprise zinc.

Particles comprising different material may have different size and mass range for the largest acceptable particle. For example, the largest acceptable particle comprising acrylic that may be found in a darbepoetin composition can have an L, W and M of no more than about 302 μm, about 184 μm, and about 11 μg, respectively, while the largest acceptable particle comprising cellulose that may be found in a darbepoetin composition can have an L, W, and M of no more than about 479 μm, about 127 μm, and about 11.6 μg, respectively. Specific examples of the types of particles that may be found in a darbepoetin composition, the size and mass of the largest acceptable particle for each type as well as the toxicology assessment and medical opinion for the largest acceptable particle for each type are shown in Example 2 below.

In some embodiments of the method, different particles of the one or more particles identified in the composition comprising darbepoetin may comprise different types materials, e.g., some particles of the one or more particles comprise acrylate and some particles of the one or more particles comprise aluminum, the composition is acceptable if the largest particle of each type has a L, W and M that is within the range disclosed herein for that type of particle, e.g., the largest of the acrylate particles has a L of no more than about 302 μm, a W of no more than about 184 μm, and a M of no more than 11 μg, and the largest of the aluminum particles has a L of no more than about 74 μm, a W of no more than about 28 μm, and a M of no more than about 0.14 μg.

In one embodiment, the injectable pharmaceutical composition comprising darbepoetin is a solution for subcutaneous administration. In another embodiment, the injectable pharmaceutical composition comprising darbepoetin is a solution for intravenous administration.

Injectable Pharmaceutical Compositions Comprising Pegfilgrastim

In some embodiments, the injectable pharmaceutical composition comprises pegfilgrastim. In one embodiment, particles that may be found in a pegfilgrastim composition comprise any one of the following: aluminum silicate, calcium carbonate, iron, polytetrafluorocarbon and poly(ethylacrylate), polystyrene, polysulfone, poly(isobutylene)-butyl rubber, rubber, silicate, silicone, or stainless steel. In one embodiment, particles that may be found in a pegfilgrastim composition may comprise any one of aluminum silicate, calcium carbonate, iron, polytetrafluorocarbon and poly(ethylacrylate), polystyrene, polysulfone, poly(isobutylene)-butyl rubber, rubber, silicate, or silicone. In one embodiment, particles that may be found in a pegfilgrastim composition comprises aluminum, calcium carbonate, or polystrene.

One or more particles may be found in an injectable pegfilgrastim composition. The composition is acceptable as long as the size (e.g., length and width) and mass of the largest particle of the one or more particles is within a certain range. Exemplary size and mass of the largest particle that may be acceptable in a pegfilgrastim composition include that the particle has a L of no more than about 3,547 μm, a W of no more than about 430 μm, and a M of no more than about 5,160 μg; or that the particle has a L of no more than about 931 μm, a W of no more than about 319 μm, and a M of no more than about 278 μg; or that the particle has a L of no more than about 488 μm, a W of no more than about 262 μm, and a M of no more than about 35.5 μg; or that the particle has a L of no more than about 931 μm, a W of no more than about 319 μm, and a M of no more than about 144 μg; or that the particle has a L of no more than about 137 μm, a W of no more than about 108 μm, and a M of no more than about 3.5 μg; or that the particle has a L of no more than about 137 μm, a W of no more than about 108 μm, and a M of no more than about 1.8 μg; or that the particle has a L of no more than about 209 μm, a W of no more than about 79 μm, and a M of no more than about 0.34 μg; or that the particle has a L of no more than about 209 μm, a W of no more than about 79 μm, and a M of no more than about 1.1 μg; or that the particle has a L of no more than about 488 μm, a W of no more than about 262 μm, and a M of no more than about 35.5 μg; or that the particle has a L of no more than about 122 μm, a W of no more than about 105 μm, and a M of no more than about 1.7 μg; or that the particle has a L of no more than about 486 μm, a W of no more than about 312 μm, and a M of no more than about 54.5 μg; or that the particle has a L of no more than about 978 μm, a W of no more than about 166 μm, and a M of no more than about 1,246.6 μg.

In some embodiment, the invention disclosed herein comprises a method of making an injectable pharmaceutical composition comprising pegfilgrastim, the method comprises detecting the presence of one or more particles in the composition, analyzing the size of the particles and the materials comprised in the particles, and accepting the injectable pharmaceutical composition if the largest particle of the one or more particles has a L of no more than about 3,547 μm, a W of no more than about 430 μm, and a M of no more than about 5,160 μg, and the one or more particles comprise aluminum, calcium carbonate, iron, polytetrafluorocarbon andpoly(ethylacrylate), polystyrene, polysulfone, poly(isobutylene)-butyl rubber, rubber, silicate, silicone, or stainless steel. In some embodiments of the method, the injectable composition comprising pegfilgrastim is acceptable if the largest particle of the one or more particles found in the composition has a L of no more than about 930 μm, a W of no more than about 320 μm, and a M of no more than about 280 μg and the one or more particles comprise aluminum, calcium carbonate, polytetrafluorocarbon and poly(ethylacrylate), polystyrene, polysulfone, poly(isobutylene)-butyl rubber, rubber, silicate, or silicone.

In some embodiments of the method, the injectable composition comprising pegfilgrastim is acceptable if the largest particle of the one or more particles found in the composition has a L of no more than about 209 μm, a W of no more than about 79 μm, and a M of no more than about 0.34 μg, and the one or more particles comprise aluminum silicate. In some embodiments of the method, the injectable composition comprising pegfilgrastim is acceptable if the largest particle of the one or more particles found in the composition has a L of no more than about 931 μm, a W of no more than about 319 μm, and a M of no more than about 278 μg, and the one or more particles comprises calcium carbonate. In some embodiments of the method, the injectable composition comprising pegfilgrastim is acceptable if the largest particle of the one or more particles found in the composition has a L of no more than about 3,547 μm, a W of no more than about 430 μm, and a M of no more than about 5,160 μg, and the one or more particles comprise iron. In some embodiments of the method, the injectable composition comprising pegfilgrastim is acceptable if the largest particle of the one or more particles found in the composition has a L of no more than about 137 μm, a W of no more than about 108 μm, and a M of no more than about 3.5 μg polytetrafluorocarbon and no more than about 1.8 μg poly(ethylacrylate), and the one or more particles comprise polytetrafluorocarbon and poly(ethylacrylate). In some embodiments of the method, the injectable composition comprising pegfilgrastim is acceptable if the largest particle of the one or more particles found in the composition has a L of no more than about 488 μm, a W of no more than about 262 μm, and a M of no more than about 35.5 μg, and the one or more particles comprise polystyrene. In some embodiments of the method, the injectable composition comprising pegfilgrastim is acceptable if the largest particle of the one or more particles found in the composition has a L of no more than about 122 μm, a W of no more than about 105 μm, and a M of no more than about 1.7 μg, and the one or more particles comprises polysulfone. In some embodiments of the method, the injectable composition comprising pegfilgrastim is acceptable if the largest particle of the one or more particles found in the composition has a L of no more than about 209 μm, a W of no more than about 79 μm, and a M of no more than about 1.1 μg, and the one or more particles comprise poly(isobutylene)-buty rubber. In some embodiments of the method, the injectable composition comprising pegfilgrastim is acceptable if the largest particle of the one or more particles found in the composition has a L of no more than about 931 μm, a W of no more than about 319.4 μm, and a M of no more than about 144 μg, and the one or more particles comprise rubber. In some embodiments of the method, the injectable composition comprising pegfilgrastim is acceptable if the largest particle of the one or more particles found in the composition has a L of no more than about 931 μm, a W of no more than about 319 μm, and a M of no more than about 144 μg, and the one or more particles comprise silicate. In some embodiments of the method, the injectable composition comprising pegfilgrastim is acceptable if the largest particle of the one or more particles found in the composition has a L of no more than about 486 μm, a W of no more than about 312 μm, and a M of no more than about 54.5 μg, and the one or more particles comprise silicone. In some embodiments of the method, the injectable composition comprising pegfilgrastim is acceptable if the largest particle of the one or more particles found in the composition has a L of no more than about 978 μm, a W of no more than about 166 μm, and a M of no more than about 1246.6 μg, and the one or more particles comprise stainless steel.

Particles comprising different material may have different size and mass range for the largest acceptable particle. For example, the largest acceptable particle comprising calcium carbonate that may be found in a pegfilgrastim composition can have an L, W and M of no more than about 931 μm, about 319 μm, and about 278 μg, respectively, while the largest acceptable particle comprising iron that may be found in a pegfilgrastim composition can have an L, W, and M of no more than about 3,547 μm, about 430 μm, and about 5,160 μg, respectively. Specific examples of the types of particles that may be found in a pegfilgrastim composition, the size and mass of the largest acceptable particle for each type as well as the toxicology assessment and medical opinion of the largest acceptable particle for each type are shown in Example 3 below. In one embodiment, the injectable pharmaceutical composition comprising pegfilgrastim is a solution for subcutaneous administration.

In some embodiments of the method, different particles of the one or more particles identified in the composition comprising pegfilgrastim may comprise different types of materials, e.g., some particles of the one or more particles comprise aluminum silicate and some particles of the one or more particles comprise calcium carbonate, the composition is acceptable if the largest particle of each type has a L, W and M that is within the range disclosed herein for that type of particle, e.g., the largest of the aluminum silicate particles has a L of no more than about 209 μm, a W of no more than about 79 μm, and a M of no more than about 0.3 μg, and the largest of the calcium carbonate particles has a L of no more than about 931 μm, a W of no more than about 319 μm, and a M of no more than about 278 μg.

The injectable pharmaceutical composition may be prepared by methods known and established in the art. For example, the polypeptide or antibody comprised in the injectable pharmaceutical composition may be synthesized by techniques known in the art, including recombinant techniques, peptide synthesis, isolation from an endogenous source of the protein, or a combination thereof. In one embodiment, the polypeptide or antibody is synthesized by recombinant techniques include expression in prokaryotic (e.g., *E. coli*) or eukaryotic (e.g., CHO) cells. The polypeptide or antibody is then purified from a heterogeneous mix of proteins using various purification steps including one or more of following: viral inactivation steps, numerous chromatography and filtration steps including affinity chromatography, cation exchange chromatography, anion exchange chromatography, hydrophobic interaction chromatography, multi-modal chromatography, hydroxyapatite chromatography, ultrafiltration and diafiltration, single pass tangential flow filtration (SPTFF), and depth filtration, to remove impurities such as host cell proteins. The purified polypeptide or antibody is formulated with appropriate excipients to make the final formulation and then filled into appropriate containers (e.g., vial, ampule, syringe or auto-injector), which are inspected and analyzed for particles.

Methods for Detecting Particles in Injectable Pharmaceutical Compositions

Particles in injectable pharmaceutical compositions may be detected or identified by various methods known and established in the art including manual and automated methods. In one embodiment, particles in an injectable pharmaceutical composition are detected or identified by manually inspecting the injectable composition. The conditions for manual inspection are specified in USP <790>, the content of which is incorporated herein by reference. If a composition is stored in a temperature controlled environment, it is kept at room temperature until the external surface of the container comprising the composition becomes clear and free of condensation before commencing inspection. Before inspection, dust and/or stains are removed from the external surface of the container using an appropriate wipe, e.g., a low particulate wipe that is either dry or dampened with 70% isopropanol alcohol. Specifically in manual inspection, an injectable pharmaceutical composition is inspected under a light intensity of between 2,000 and 3,750 lux. In one embodiment, the light intensity used for inspection is between 3,500 and 3,750 lux. This can be achieved through the use of two 13-W or 15-W fluorescent lamps (e.g., F13/T5 or F15/T8). Other light sources (e.g., incandescent, LED) may also be used as long as they provide illumination at the point of inspection within the specified intensity range. The sample is then examined without magnification against a black background and against a white background for at least five (5) seconds per background. During the inspection process, the sample may be inverted and/or swirled slowly (to avoid causing gas bubbles) and observed against each background for the presence of particles.

In one embodiment, particles in an injectable pharmaceutical composition are detected or identified using semi-automatic or automatic methods, e.g., semi-automatic or automatic systems that are commercially available for identifying particles in pharmaceutical compositions. Semi-automatic inspection systems that may be used for detecting particles in injectable pharmaceutical compositions include the Seidenader semi-automatic inspection machine. Automatic systems that may be used for this purpose include the Seidenader De-/Re-Nester DE.SY.RE, the Seidenader VI series, the Seidenader MS series, the Seidenader ES series, the Seidenader CS series and the Seidenader MS-S/VI-S series machines. Other instruments or apparatus that may be used for detecting particles in injectable pharmaceutical compositions include particle counting systems such as the APS S 200 particle counting system (e.g., LiQuilaz Particle Counter), the ParticleScope™ particle measurement system (Phoenix Imaging, Ltd.), and coulter counters (e.g., Multisizer 3 coulter counter by Beckman Coulter Life Sciences).

Characterization of Particles

Once a particle from the statistical sampling is identified in an injectable composition and its presence confirmed, it is then characterized to determine its physical and chemical properties using methods established and well known in the art. Physical properties (e.g., L, W and H) of a particle may be characterized using microscopic tools such as high powered microscope and Scanning Electron Microscopy (SEM). Specifically, the particle is removed or isolated from the injectable composition using cleaned probes or filtered onto filters and then viewed optically using a high powered microscope or SEM, which is connected to a computer that has an appropriate software package. Images of the particle are taken using the microscope and dimensions of the particle are measured using the software package. Typically, the longest dimension from end to end of the particle is assigned as the length, the second longest dimension from end to end of the particle is assigned as the width, and the third longest dimension from end to end of the particle is assigned as the height. The dimension measurements along with the images of the particle are reported.

Chemical properties of a particle (e.g., materials comprised in the particle) are typically characterized using various spectroscopic analysis methods that provide a characteristic spectrum reflecting the material(s) comprised in the particle. This characteristic spectrum is then compared to a library of spectra of known materials to determine the identity of the material(s) comprised in the particle. Non-limiting spectroscopic analysis methods that may be used for characterizing the chemical properties of a particle include SEM, Fourier Transform Infrared Spectroscopy (FTIR), Raman imaging, and laser-induced breakdown spectroscopy (LIBS). Standard spectrum libraries of known materials and algorithm software for comparison and identification of the materials comprised in a particle are readily available in the art (e.g., provided by manufactures of the spectroscopic machines, or third party software suppliers).

By way of illustration, to identify the chemical composition of a particle found in an injectable pharmaceutical composition, the particle is analyzed using a spectroscopic method such as FTIR to generate a characteristic spectrum reflecting the materials comprised in the particle. This characteristic spectrum is then compared to a library of FTIR spectra of known materials and found to match the spectrum of cellulose. Based on the match, the particle is identified as comprising cellulose.

Calculation of the Mass of a Particle

The mass of a particle is calculated based on the physical and chemical properties of the particle. Specifically, the mass of a particle is calculated based on the volume of the particle and the density of the material(s) comprised in the particle. The volume of the particle is calculated based on the dimensions of the particle. As particles are typically irregular in shape, worst case geometrical model is assumed when calculating the volume of particles. Specifically, if a particle is identified as having a fiber morphology, a right circular cylinder is assumed as the worst case geometrical model. The volume of the particle is calculated using the following formula: Volume $(V)=(3.1416)\times(d/2)^2\times h$, wherein "h" is equal to the length (L) of the particle and "d" is equal to the width (W) of the particle, and "V" is expressed in cubic micrometers ($\mu m^3$).

If a particle is identified as having a non-fiber morphology (e.g., residues, flat or equant particles), a cube or rectangular prism is assumed as the worst case geometrical model. The volume of the particle is calculated using the following formula: Volume (V)=Length (L)×Width (W)×Height (H), wherein if no information about H is available, the height is equal to W, and "V" is expressed in cubic micrometers ($\mu m^3$).

If a particle is identified as a cone, the volume of the particle is calculated using the following formula: Volume $(V)=(3.1416)\times(r)^2\times h/3$, wherein "r" is equal to half of the width of the particle, "h" is equal to the length of the particle, and "V" is expressed in cubic micrometers ($\mu m^3$).

Cubic microcemeters may be converted to cubic centimeters for calculating the mass of a particle: $1\times10^{-12}$ $cm^3$=1 $\mu m^3$.

Density values for various materials are known in the art and can be found from scientific sources. Sources that provide material density values include Polymer Handbook (Brandrup J. et al. eds., 1999), CRC Handbook of Chemistry and Physics (e.g., Internet Version 2005, available at hbcponline), and the Hazardous Substance Database (HSDB) from the U.S. National Library of Medicine. Density values of exemplary materials that may be found in injectable pharmaceutical compositions disclosed herein are listed in Table 1 below.

TABLE 1

Density of exemplary materials

| Material | Density ($g/cm^3$) |
|---|---|
| Acrylate | 1.2 |
| Acrylic | 1.2 |
| Aliphatic Hydrocarbon | 0.7768 |
| Aluminum | 2.7 |
| Aluminum Silicate | 2.6 |
| Borosilicate Glass | 2.23 |
| Calcium Carbonate | 2.83 |
| Cellulose | 1.64 |
| Charcoal | 0.21 |
| Epoxy Resin | 1.07 |
| Hydrated Aluminum Silicate | 2.6 |
| Iron | 7.784 |
| Keratin | 1.72 |
| Magnesium | 1.738 |
| Magnesium Silicate | 2.71 |
| Natural Protein Fiber (Silk) | 1.34 |
| Natural Protein Fiber (Wool) | 1.314 |
| Nickel | 8.902 |
| Nitrocellulose | 1.23 |
| Phosphate | 1.76 |
| Poly(Isobutylene-Butyl) Rubber | 0.933 |
| Polyamide | 1.15 to 1.25[2] |
| Polyester (PET) | 1.42 |
| Polyether Ether Ketone | 1.32 |
| Polyethylacrylate | 1.12 |
| Polyethylene | 0.967 |
| Polyoxymethylene (POM) | 1.435 |
| Polystyrene | 1.065 |
| Polysulfone | 1.24 |
| Polytetrafluorocarbon | 2.16 |
| Polytetrafluoroethylene (PTFE) | 2.2 |
| Polyurethane | 1.2 |
| Polyvinyl Chloride (PVC) | 1.392 |
| Rubber | 1.19 To 1.25[2] |
| Silicate | 2.23 |
| Silicon Carbide | 3.16 |
| Silicone | 1.11 To 1.20[2] |
| Stainless Steel | 7.9 |
| Titanium | 4.54 |
| Zinc | 7.133 |

The mass of a particle is calculated using the following formula: Mass (M)=V×D, wherein "V" is the volume of the particle and "D" is the density of the material comprised in the particle. If a particle is identified as comprising a single material, the particle is considered as constituting 100% of the identified material and the density of that material is used for calculating the mass. If a particle is identified as comprising multiple materials, the particle is considered as constituting 100% of each of the identified materials and the density of each of the materials is used for calculating the mass. If the particle is identified as multiple fragments of a single material, the mass is the sum of the mass of each fragment, wherein the mass of each fragment is calculated using the volume of that fragment and the density of the material.

The methods disclosed herein can be used for inspecting or detecting the presence of one or more particles in injectable pharmaceutical compositions, analyzing the dimensions and the materials comprised in the particles, calculating the mass of the particles, and accepting the compositions if the size and mass of the largest of the one or more particles are within a range disclosed herein.

The invention will be more fully understood by reference to the following examples. The examples should not, however, be construed as limiting the scope of the invention.

EXAMPLES

Example 1. Compilation of Particles Historically Detected in Injectable Compositions Comprising Etanercept Table 2 below lists the largest particles that have been detected during visual inspection of injectable pharmaceutical compositions comprising etanercept, their physical and chemical properties (e.g., size, material composition, mass), as well as the toxicological assessment and medical opinion for the particles. As shown in the table, it has been concluded that each of the particles raises little toxicological concern and poses low to negligible safety risk when administered to patients. An etanercept composition comprising one or more particles is considered to be acceptable as long as the size and mass of the largest of the one or more particles for each type are no more than about the size and mass of the corresponding largest particle shown in Table 2.

TABLE 2

Largest particles that have been identified in injectable pharmaceutical compositions comprising etanercept

| Particle type | Source | Largest size (μm) | Calculated mass | Toxicology assessment | Medical opinion |
|---|---|---|---|---|---|
| Acrylic | Extrinsic | L: 257 μm/ W: 133 μm | 5.4 μg | Not a toxicological concern. | The potential risk to patients from a pre-filled syringe (PFS) containing a particle of this type is very low. |

TABLE 2-continued

Largest particles that have been identified in injectable pharmaceutical compositions comprising etanercept

| Particle type | Source | Largest size (μm) | Calculated mass | Toxicology assessment | Medical opinion |
|---|---|---|---|---|---|
| Aluminim | Extrinsic | L: 420 μm/ W: 225 μm | <0.001 μg | Not a toxicological concern. | The potential risk to patients from a vial containing a particle of this type is very low to negligible. |
| Aliphatic Hydrocaron | Extrinsic | L: 131 μm/ W: 64 μm | 0.42 μg | Exposure to low level of this polymer is not a toxicological concern. | The potential risk to patients from a PFS containing a particle of this type is very low. |
| Charcoal | Extrinsic | L: 176 μm/ W: 110 μm | 2.87 μg | Not a toxicological concern. | The potential risk to patients from a syringe containing a particle of this type is considered to be very low to negligible. |
| Borosilicate Glass | Extrinsic/ Intrinsic | L: 5047 μm/ W: 2939 μm | 97,200 μg | Not a toxicological concern. | The potential risk to patients from a syringe containing a particle of this type is very low. |
| Natural Protein Fibre (Wool/Silk) | Extrinsic | L: 19200 μm/ W: 50 μm | 49.50 (wool) μg/50.50 (silk) μg | Not a toxicological concern. | The potential risk to patients from a PFS containing a particle of this type is very low. |
| Polyester (PET) | Extrinsic | L: 2388 μm/ W: 67 μm | 14.7 μg | Not a toxicological concern. | The potential risk to patients from a PFS containing a particle of this type is very low. |
| Polyurethane | Extrinsic | L: 359 μm/ W: 306 μm | 21.0 μg | Not a toxicological concern. | PFSs containing polyurethane particle would pose a very low risk to patients. |
| Polyether Ether Ketone | Extrinsic | L: 5150 μm/ W: 300 μm | 2330 μg | Not a toxicological concern. | Very low potential risk to patients. |
| Polytetrafluoroethylene (PTFE) | Intrinsic | L: 700 μm/ w: 250 μm | 45.9 μg | Not a toxicological concern. | The potential risk to patients from a vial containing the particle identified is very low to negligible |
| Polyoxymethylene (POM) | Extrinsic | L: 1891.8 μm/ W: 596.82 μm | 1,010.00 μg | Not a toxicological concern. | The potential risk to patients from a PFS containing a particle of this type is very low to negligible. |
| Polystyrene | Extrinsic | L: 6154 μm/ W: 2454 μm | 39,300 μg | Not a toxicological concern. | The potential risk to patients from a PFS containing a particle of this type is very low to negligible. |
| Silicon Carbide | Extrinsic | L: 359 μm/ W: 306 μm | 48.7 μg | Not a toxicological concern. | The potential risk to patients from a PFS containing a particle of this type is very low. |
| Stainless Steel | Intrinsic | L: 450 μm/ W: 400 μm | 72.00 μg | Not a toxicological concern. | The potential risk to patients from a PFS containing a particle of this type is very low. |

Example 2. Compilation of Particles Historically Detected in Injectable Compositions Comprising Darbepoetin Table 3 below lists the largest particles that have been detected during visual inspection of injectable pharmaceutical compositions comprising darbepoetin, their physical and chemical properties (e.g., size, material composition, mass), as well as the toxicological assessment and medical opinion for the particles. As shown in the table, it has been concluded that each of the particles raises little toxicological concern and poses low to negligible safety risk when administered to patients. A darbepoetin composition comprising one or more particles is considered to be acceptable as long as the size and mass of the largest particle of the one or more particles of each type are no more than about the size and mass of the corresponding largest particle in Table 3.

TABLE 3

Largest particles that have been identified in injectable pharmaceutical compositions comprising darbepoetin

| Particle type | Source | Largest size (μm) | Calculated mass (μg) | Toxicology assessment | Medical opinion |
|---|---|---|---|---|---|
| Acrylate | Extrinsic | L: 302 μM/ W: 184 μm | 11.00 μg | Not a toxicological concern. | The potential risk to patients from a PFS containing a particle of this type is very low. |
| Aluminum | Extrinsic | L: 74 μm/ W: 28 μm | 0.14 μg | Not a toxicological concern. | The potential risk to patients from a PFS containing a particle of this type is very low. |
| Cellulose | Extrinsic | L:479pm/ W: 127pm | 11.6 μg | Not a toxicological concern. | The potential risk to patients from a PFS containing a particle of this type is low to very low. |
| Epoxy Resin | Extrinsic | L: 442 μm/ W: 237μm | 60.00 μg | Not a toxicological concern. | The potential risk to patients from a PFS containing a particle of this type is very low. |
| Borosilicate Glass | Extrinsic/ Intrinsic | L: 2304 μm/ W: 1790 μm | 21,190 μg | Not a toxicological concern. | The potential risk to patients from a syringe containing a particle of this type is very low. |
| Hydrated Aluminium Silicate | Extrinsic | L: 515 μm/ W: 509 μm | 357.75 μg | Not a toxicological concern. | The potential risk to patients from a syringe containing a particle of this type is very low. |
| Iron (Fe) | Extrinsic | L: 74 μm/ W: 28 μm | 0.05 μg | Not a toxicological concern. | The potential risk to patients from a syringe containing a particle of this type is very low. |
| Iron and Nickel rich material with Phosphate | Extrinsic (Iron and Nickel)/ Intrinsic (Phosphate) | L: 904 μm/ W: 10 μm/ H: 412 μm | 3.04 μg (Fe)/ 19.10 μg (Ni)/ 6.56 μg (Phosphate) | Not a toxicological concern. | The potential risk to patients from a syringe containing a particle of this type is very low. |
| Keratin | Extrinsic | L: 81 μm/ W: 44 μm | 212.00 μg | Largest exposure to this particle is not toxicological concern. | The potential risk to patients from a syringe containing a particle of this type is very low. |
| Magnesium | Extrinsic | L: 836 μm/ W: 120 μm | 1.05 μg | Not a toxicological concern. | The potential risk to patients from a syringe containing a particle of this type is very low. |
| Magnesium Silicate | Extrinsic | L: 681 μm/ W: 390 μm | 398.00 μg | Not a toxicological concern. | The potential risk to patients from a syringe containing a particle of this type is very low. |
| Nitrocellulose | Extrinsic | L: 471 μm/ W: 333 μm | 64.20 μg | Not a toxicological concern. | The potential risk to patients from a PFS containing a particle of this type is very low. |
| Polyamide (Nylon) | Extrinsic | L: 1331 μm/ W: 293 μm | 130.00 μg | Not a toxicological concern. | The potential risk to patients from a PFS containing a |

TABLE 3-continued

| Particle type | Source | Largest size (μm) | Calculated mass (μg) | Toxicology assessment | Medical opinion |
|---|---|---|---|---|---|
| | | | | | particle of this type is very low. |
| Polyurethane | Extrinsic | L: 570 μm/ W: 321 μm | 130.00 μg | Not a toxicological concern. | PFSs containing polyurethane particle would pose a very low risk to patients. |
| Polyethylene | Extrinsic | L: 4530 μm/ W: 8890 μm | 764 μg | Not a toxicological concern. | The potential risk to patients from a vial containing the particle identified is very low to negligible. |
| Polytetrafluoroethyle ne (PTFE) | Intrinsic | L: 129 μm/ W: 93 μm | 2.41 μg | Not a toxicological concern. | The potential risk to patients from a vial containing the particle identified is very low to negligible. |
| Polyvinyl Chloride (PVC) | Extrinsic | L: 1265 μm/ W: 322 μm | 181.00 μg | Not a toxicological concern. | The potential risk to patients from a PFS containing a particle of this type is very low to negligible. |
| Stainless Steel | Intrinsic | L: 254 μm/ W: 190 μm | 72.9 μg | Not a toxicological concern. | The potential risk to patients from a PFS containing a particle of this type is very low. |
| Titanium | Intrinsic | L: 1331 μm/ W: 174 μm/ H: 889 μm | 926.00 μg | Not a toxicological concern. | The potential risk to patients from a PFS containing a particle of this type is very low to negligible |
| Zinc | Intrinsic | L: 836 μm/ W: 120 μm | 4.29 μg | Not a toxicological concern. | The potential risk to patients from a PFS containing a particle of this type is very low. |

Largest particles that have been identified in injectable pharmaceutical compositions comprising darbepoetin

Example 3. Compilation of Particles Historically Detected in Injectable Compositions Comprising Pegfilgrastim Table 4 below lists the largest particles that have been detected during visual inspection of injectable pharmaceutical compositions comprising pegfilgrastim, their physical and chemical properties (e.g., size, material composition, mass), as well as the toxicological assessment and medical opinion for the particles. As shown in the table, it has been concluded that each of the particles raises little toxicological concern and poses low to negligible safety risk when administered to patients. A pegfilgrastim composition comprising one or more particles is considered to be acceptable as long as the size and mass of the largest particle of the one or more particles of each type are no more than about the size and mass of the corresponding largest particle in Table 4.

Table 4. Largest particles that have been identified in injectable pharmaceutical compositions comprising pegfilgrastim

TABLE 4

Largest particles that have been identified in injectable pharmaceutical compositions comprising pegfilgrastim

| Particle type | Source | Largest size (μm) | Calculated mass (mg) | Toxicology assessment | Medical opinion |
|---|---|---|---|---|---|
| Aluminium Silicate | Extrinsic | L: 209 μm/ W: 79 μm | 0.34 μg | Not a toxicological concern. | The potential risk to patients from a PFS containing a particle of this type is very low. |
| Calcium Carbonate | Extrinsic | L: 931 μm/ W:319 μm | 278.00 μg | Not a toxicological concern. | The potential risk to patients from a syringe containing a particle of this type is very low. |

TABLE 4-continued

Largest particles that have been identified in injectable pharmaceutical compositions comprising pegfilgrastim

| Particle type | Source | Largest size (μm) | Calculated mass (mg) | Toxicology assessment | Medical opinion |
|---|---|---|---|---|---|
| Iron (Fe) | Extrinsic | L: 3547 μm/ W: 430 μm | 5160 μg | Not a toxicological concern. | The potential risk to patients from a PFS containing a particle of the type described is very low. |
| Polytetrafluorocarbon and a Poly (ethylacrylate) | Intrinsic: Polytetrafluorocarbon Extrinsic: Poly (ethylacrylate) | L: 137 μm/ W: 108 μm | 3.45 μg/1.79 μg | Not a toxicological concern. | The potential risk to patients from a PFS containing a particle of this type is very low. |
| Polystyrene | Extrinsic | L: 488 μm/ W: 262 μm | 35.51 μg | Largest exposure to this particle is not toxicological concern. | The potential risk to patients from a PFS containing a particle of this type is very low. |
| Polysulfone | Extrinsic | L: 122 μm/ W: 105 μm | 1.68 μg | Not a toxicological concern. | The potential risk to patients from a PFS containing a particle of this type is very low. |
| Poly(isobutylene)-Butyl Rubber | Extrinsic | L: 209 μm/ W: 79 μm | 1.08 μg | Not a toxicological concern. | The potential risk to patients from a PFS containing a particle of this type is very low. |
| Rubber | Extrinsic | L: 930.7 μm/ W: 319.4 μm | 144.00 μg | Not a toxicological concern. | The potential risk to patients from a PFS containing a particle of this type is very low. |
| Silicate | Extrinsic | L: 931 μm/ W: 319 μm | 144.00 μg | Not a toxicological concern. | The potential risk to patients from a PFS containing a particle of this type. |
| Silicone | Intrinsic | L: 486 μm/ W: 312 μm | 54.50 × 10−6 g | Exposure to silicone was significantly below their respective PDE's. Exposure to low levels of this polymer is not toxicological concern. | The potential risk to patients from a PFS containing a particle of this type is very low. |
| Stainless Steel | Intrinsic/ Extrinsic | L: 978 μm/ W: 166 μm | 1,246.58 μg | Not a toxicological concern. | The potential risk to patients from a PFS containing the particle identified is very low to negligible. |

Example 4. Identification and Characterization of a Particle Detected in an Injectable Pharmaceutical Composition Comprising Etanercept A particle was identified in an injectable composition comprising etanercept in a syringe using the manual inspection method disclosed herein. The particle in the syringe was investigated and analyzed for its physical and chemical properties. The particle was imaged, measured and identified as Acrylic. The dimensions of the particle was found to be as the following: a). Length (L)=200 μm and b). Width (W)=100 μm. To calculate the volume of the particle, it was assumed that the particle has a worst case geometry of a rectangular prism. As no information was available on the height of the particle, the third dimension was considered equal to its width: Height (H)=100 μm.

The volume of the particle was therefore calculated using the formula: Volume (V)=L×W×H, which was 200 μm×100 μm×100 μm=$2\times10^{6}$ $\mu m^{3}$=$2\times10^{-6}$ $cm^{3}$. As the density (d) of Acrylic is 1.2 $g/cm^{3}$, the mass of the particle was calculated as Mass (M)=V×d=$2\times10^{-6}$ $cm^{3}\times1.2$ $g/cm^{3}$=2.4 μg.

Table 2 above indicates that for acrylic particles found in an injectable pharmaceutical composition comprising etanercept, the size of the largest particle was L:257 μm and W:133 μm, and the calculated mass was 5.4 μg. In addition, the largest particle was considered not a toxicological concern and to have a very low risk to patients. As the size and mass of the particle identified this case was smaller than that of the largest acrylic particle, the overall patient risk is considered as low. Consequently, the etanercept composition in the syringe is considered to be acceptable.

What is claimed is:

1. A method of making an injectable pharmaceutical composition comprising etanercept, the method comprises:

detecting the presence of one or more particles in an injectable composition comprising etanercept, analyzing the size of the particles and the materials comprised in the particles, and accepting the injectable pharmaceutical composition comprising etanercept if the largest particle of the one or more particles has a length (L) of no more than about 19,200 μm, a width (W) of no more than about 2,939 μm, and a mass (M) of no more than about 97,200 μg, wherein the one or more particles comprise acrylic, aluminum, aliphatic hydrocarbon, charcoal, borosilicate glass, wool and silk, polyester (PET), polyurethane, polyether ether ketone, polytetrafluoroethylene (PTFE), polyoxymethylene (POM), polystyrene, silicon carbide, or stainless steel.

2. The method of claim 1, wherein (a) the largest particle of the one or more particles has a L of no more than about 257 μm, a W of no more than about 133 μm, and a M of no more than about 5.4 μg, and the one or more particles comprise acrylic;

(b) the largest particle of the one or more particles has a L of no more than about 420 μm, a W of no more than about 225 μm, and a M of no more than about 0.001 μg, and the one or more particles comprise aluminum;

(c) the largest particle of the one or more particles has a L of no more than about 131 μm, a W of no more than about 64 μm, and a M of no more than about 0.42 μg, and the one or more particles comprise aliphatic hydrocarbon;

(d) the largest particle of the one or more particles has a L of no more than about 176 μm, a W of no more than about 110 μm, and a M of no more than about 2.9 μg, and the one or more particles comprise charcoal;

(e) the largest particle of the one or more particles has a L of no more than about 5,047 μm, a W of no more than about 2,939 μm, and a M of no more than about 97,200 μg, and the one or more particles comprise borosilicate glass;

(f) the largest particle of the one or more particles has a L of no more than about 19,200 μm, a W of no more than about 50 μm, and a M of no more than about 50 μg wool and no more than about 50 μg silk, and the one or more particles comprise natural protein fiber;

(g) the largest particle of the one or more particles has a L of no more than about 2,388 μm, a W of no more than about 67 μm, and a M of no more than about 14.7 μg, and the one or more particles comprise polyester;

(h) the largest particle of the one or more particles has a L of no more than about 359 μm, a W of no more than about 306 μm, and a M of no more than about 21 μg, and the one or more particles comprise polyurethane;

(i) the largest particle of the one or more particles has a L of no more than about 5,150 μm, a W of no more than about 300 μm, and a M of no more than about 2,330 μg, and the one or more particles comprise polyether ether ketone;

(j) the largest particle of the one or more particles has a L of no more than about 700 μm, a W of no more than about 250 μm, and a M of no more than about 45.9 μg, and the one or more particles comprise PTFE;

(k) the largest particle of the one or more particles has a L of no more than of about 1,891 μm, a W of no more than about 596.8 μm, and a M of no more than about 1,010 μg, and the one or more particles comprise POM;

(l) the largest particle of the one or more particles has a L of no more than of about 6,154 μm, a W of no more than about 2,454 μm, and a M of no more than about 39,300 μg, and the one or more particles comprise polystyrene;

(m) the largest particle of the one or more particles has a L of no more than of about 359 μm, a W of no more than about 306 μm, and a M of no more than about 48.7 μg, and the one or more particles comprise silicon carbide; or (n) the largest particle of the one or more particles has a L of no more than of about 450 μm, a W of no more than about 400 μm, and a M of no more than about 72 μg, and the one or more particles comprise stainless steel.

3. The method of claim 1, wherein the injectable pharmaceutical composition is suitable for subcutaneous administration.

4. A method of making an injectable pharmaceutical composition comprising darbepoetin, the method comprises:

detecting the presence of one or more particles in an injectable composition comprising darbepoetin, analyzing the size of the particles and the materials comprised in the particles, and accepting the injectable pharmaceutical composition comprising darbepoetin if the largest particle of the one or more particles has a L of no more than about 4,530 μm, a W of no more than about 8,890 μm, and a M of no more than about 21,190 μg, wherein the one or more particles comprise acrylate, aluminum, cellulose, epoxy resin, keratin, hydrated aluminum silicate, magnesium, magnesium silicate, nitrocellulose, polyurethane, polytetrafluoroethylene (PTFE), stainless steel, zinc, borosilicate glass, iron, iron and nickel rich material with phosphate, polyamide, polyethylene, polyvinyl chloride (PVC), or titanium.

5. The method of claim 4, wherein (a) the largest particle of the one or more particles has a L of no more than about 302 μm, a W of no more than about 184 μm, and a M of no more than 11 μg, and the one or more particles comprise acrylate;

(b) the largest particle of the one or more particles has a L of no more than about 74 μm, a W of no more than about 28 μm, and a M of no more than about 0.14 μg, and the one or more particles comprise aluminum;

(c) the largest particle of the one or more particles has a L of no more than about 479 μm, a W of no more than about 127 μm, and a M of no more than about 11.6 μg, and the one or more particles comprise cellulose;

(d) the largest particle of the one or more particles has a L of no more than about 442 μm, a W of no more than about 237 μm, and a M of no more than about 60 μg, and the one or more particles comprise epoxy resin;

(e) the largest particle of the one or more particles has a L of no more than about 2,034 μm, a W of no more than about 1,790 μm, and a M of no more than about 21,190 μg, and the one or more particles comprise borosilicate glass;

(f) the largest particle of the one or more particles has a L of no more than about 904 μm, a W of no more than about 10 μm, a H of no more than about 412 μm, and a M of no more than about 3 μg iron, no more than about 19.1 μg nickel, and no more than about 6.6 μg phosphate, and the one or more particles comprise iron and nickel rich material with phosphate;

(g) the largest particle of the one or more particles has a L of no more than about 81 μm, a W of no more than about 44 μm, and a M of no more than about 212 μg, and the one or more particles comprise keratin;

(h) the largest particle of the one or more particles has a L of no more than about 515 μm, a W of no more than about 509 μm, and a M of no more than about 357.8 μg, and the one or more particles comprise hydrated aluminum silicate;

(i) the largest particle of the one or more particles has a L of no more than about 836 μm, a W of no more than about 120 μm, and a M of no more than about 1 μg, and the one or more particles comprise magnesium;

(j) the largest particle of the one or more particles has a L of no more than about 681 μm, a W of no more than about 390 μm, and a M of no more than about 398 μg, and the one or more particles comprise magnesium silicate;

(k) the largest particle of the one or more particles has a L of no more than about 471 μm, a W of no more than about 333 μm, and a M of no more than about 64.2 μg, and the one or more particles comprise nitrocellulose;

(l) the largest particle of the one or more particles has a L of no more than about 1,331 μm, a W of no more than about 293 μm, and a M of no more than about 130 μg, and the one or more particles comprise polyamide;

(m) the largest particle of the one or more particles has a L of no more than about 570 μm, a W of no more than about 321 μm, and a M of no more than about 130 μg, and the one or more particles comprise polyurethane;

(n) the largest particle of the one or more particles has a L of no more than about 4,530 μm, a W of no more than about 8,890 μm, and a M of no more than about 764 μg, and the one or more particles comprise polyethylene;

(o) the largest particle of the one or more particles has a L of no more than about 129 μm, a W of no more than about 93 μm, and a M of no more than about 2.4 μg, and the one or more particles comprise PTFE;

(p) the largest particle of the one or more particles has a L of no more than about 322 μm, and a M of no more than about 181 μg, and the one or more particles comprise PVC;

(q) the largest particle of the one or more particles has a L of no more than about 254 μm, a W of no more than about 190 μm, and a M of no more than about 72.9 μg, and the one or more particles comprise stainless steel;

(r) the largest particle of the one or more particles has a L of no more than about 1,331 μm, a W of no more than about 174 μm, and a M of no more than about 926 μg, and the one or more particles comprise titanium; or (s) the largest particle of the one or more particles has a L of no more than about 836 μm, a W of no more than about 120 μm, and a M of no more than about 4.3 μg, and the one or more particles comprise zinc.

6. The method of claim 4, wherein the pharmaceutical composition is suitable for intravenous or subcutaneous administration.

7. A method of making an injectable pharmaceutical composition comprising pegfilgrastim, the method comprises:

detecting the presence of one or more particles in an injectable composition comprising pegfilgrastim, analyzing the size of the particles and the materials comprised in the particles, and accepting the composition comprising pegfilgrastim if the largest particle of the one or more particles has a L of no more than about 3,500 μm, a W of no more than about 430 μm, and a M of no more than about 5,100 μg, wherein the one or more particles comprise aluminum, calcium carbonate, iron, polytetrafluorocarbon, poly (ethylacrylate), polystyrene, polysulfone, poly(isobutylene)-butyl rubber, rubber, silicate, silicone, or stainless steel.

8. The method of claim 7, wherein (a) the largest particle of the one or more particles has a L of no more than about 209 μm, a W of no more than about 79 μm, and a M of no more than about 0.34 μg, and the one or more particles comprise aluminum silicate;

(b) the largest particle of the one or more particles has a L of no more than about 931 μm, a W of no more than about 319 μm, and a M of no more than about 278 μg, and the one or more particles comprises calcium carbonate;

(c) the largest particle of the one or more particles has a L of no more than about 3,547 μm, a W of no more than about 430 μm, and a M of no more than about 5,160 μg, and the one or more particles comprise iron;

(d) the largest particle of the one or more particles has a L of no more than about 137 μm, a W of no more than about 108 μm, and a M of no more than about 3.5 μg polytetrafluorocarbon and no more than about 1.8 μg poly (ethylacrylate), and the one or more particles comprise polytetrafluorocarbon and poly (ethylacrylate);

(e) the largest particle of the one or more particles has a L of no more than about 488 μm, a W of no more than about 262 μm, and a M of no more than about 35.5 μg, and the one or more particles comprise polystyrene;

(f) the largest particle of the one or more particles has a L of no more than about 122 μm, a W of no more than about 105 μm, and a M of no more than about 1.7 μg, and the one or more particles comprises polysulfone;

(g) the largest particle of the one or more particles has a L of no more than about 209 μm, a W of no more than about 79 μm, and a M of no more than about 1.1 μg, and the one or more particles comprise poly(isobutylene)-buty rubber;

(h) the largest particle of the one or more particles has a L of no more than about 931 μm, a W of no more than about 319.4 μm, and a M of no more than about 144 μg, and the one or more particles comprise rubber;

(i) the largest particle of the one or more particles has a L of no more than about 931 μm, a W of no more than about 319 μm, and a M of no more than about 144 μg, and the one or more particles comprise silicate;

(j) the largest particle of the one or more particles has a L of no more than about 312 μm, and a M of no more than about 54.5 μg, and the one or more particles comprise silicone; or (k) the largest particle of the one or more particles has a L of no more than about 978 μm, a W of no more than about 166 μm, and a M of no more than about 1246.6 μg, and the one or more particles comprise stainless steel.

* * * * *

UNITED STATES PATENT AND TRADEMARK OFFICE
CERTIFICATE OF CORRECTION

PATENT NO. : 11,576,856 B2
APPLICATION NO. : 17/050019
DATED : February 14, 2023
INVENTOR(S) : Andrew Phillip Spasoff et al.

It is certified that error appears in the above-identified patent and that said Letters Patent is hereby corrected as shown below:

In the Claims

At Column 32, Line 30, "poly (ethylacrylate)," should be -- poly(ethylacrylate), --.

At Column 32, Lines 31-32, "poly (ethylacrylate);" should be -- poly(ethylacrylate); --.

At Column 32, Line 45, "buty rubber;" should be -- butyl rubber; --.

Signed and Sealed this
Twenty-ninth Day of August, 2023

*Katherine Kelly Vidal*

Katherine Kelly Vidal
*Director of the United States Patent and Trademark Office*